United States Patent [19]

Richter et al.

[11] 4,339,381

[45] Jul. 13, 1982

[54] 1,3-ALKYLENE-DIAZETIDINE-2,4-DIONES

[75] Inventors: Reinhard H. Richter, North Haven; Benjamin W. Tucker, Bethany; Henri Ulrich, Guilford, all of Conn.

[73] Assignee: The Upjohn Company, Kalamazoo, Mich.

[21] Appl. No.: 231,876

[22] Filed: Feb. 5, 1981

[51] Int. Cl.$^3$ .................. C07D 487/06; C07D 487/08
[52] U.S. Cl. ..................... 260/239.3 B; 260/239.3 R
[58] Field of Search .................. 260/239.3 B, 239.3 R

[56] References Cited

U.S. PATENT DOCUMENTS 3,275,618  9/1966  Tilley et al. .................. 544/318
4,138,398  2/1979  Richter et al. ............... 260/239.3 R

OTHER PUBLICATIONS

Ulrich et al., "J. Organic Chemistry", vol. 29, pp. 2401-2404 (1964).
Sayigh et al., "J. Organic Chemistry", vol. 29, pp. 3344-3347 (1964).
Richter et al., "J. Org. Chem.", vol. 46 (1981), pp. 5226-5228.

Primary Examiner—Robert T. Bond
Attorney, Agent, or Firm—Denis A. Firth; John Kekich

[57] ABSTRACT

1,3-alkylene-diazetidinediones-2,4, wherein alkylene contains at least 8 carbon atoms, are described. These compounds, which can be regarded as intramolecular dimers of alkylene diisocyanates, give rise to the latter on heating. Accordingly, these compounds are useful in a variety of situations in which it is desirable to have a compound which is stable on storage in admixture with other compounds such as polyols, polyamines and the like (which latter would react with a compound containing free isocyanate groups) but which can, at any desired moment, be converted by heating to the free diisocyanate. The latter then reacts with the other component(s) of the mixture to form a polymer.

The above compounds are derived by cyclization of the appropriate cyclic allophanoyl halide.

7 Claims, No Drawings

1,3-ALKYLENE-DIAZETIDINE-2,4-DIONES

BACKGROUND OF THE INVENTION

1. Field of the Invention

This invention relates to novel heterocyclic compounds and to diisocyanates and polymers derived therefrom, and is more particularly concerned with 1,3-alkylene-diazetidinediones, with methods for their preparation, and with diisocyanates and polymers derived therefrom.

2. Description of the Prior Art

The preparation of cyclic and acyclic allophanoyl chlorides and their conversion to isocyanates is known in the art; see, for example, Ulrich et al., J. Organic Chemistry 29, 2401, 1964 and Sayigh et al., ibid p. 3344. U.S. Pat. No. 3,275,618 describes the preparation of cyclic aliphatic allophanoyl chlorides containing up to 4 carbon atoms in the alkylene chain of the ring and the conversion of these allophanoyl chlorides to the corresponding alkylene diisocyanates by heating, optionally in the presence of a tertiary amine scavenger for the hydrogen chloride which is eliminated.

It is also known that organic isocyanates readily form dimers in accordance with the following mechanism:

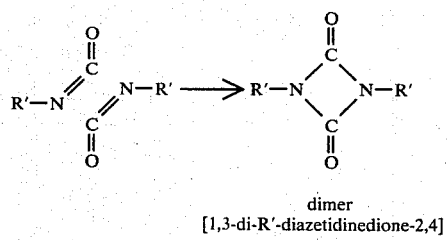

dimer
[1,3-di-R'-diazetidinedione-2,4]

However, the formation of such dimers from aliphatic diisocyanates by intramolecular (as opposed to intermolecular) condensation has not been reported previously nor has the formation of diazetidinediones from cyclic aliphatic allophanoyl chlorides. We have now found that such intramolecular dimers can be obtained from certain cyclic aliphatic allophanoyl halides and that they have valuable properties.

SUMMARY OF THE INVENTION

This invention comprises compounds having the formula:

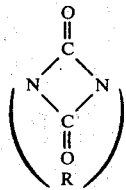

wherein R is alkylene having at least 8 carbon atoms in the chain.

The invention also comprises a process for generating the corresponding diisocyanates OCN—R—NCO (II) from the compounds of formula (I) by heating. The invention also comprises storage stable compositions which comprise a compound of formula (I) in admixture with one or more active hydrogen containing materials, which compositions, upon heating at a sufficient temperature to liberate the diisocyanate (II), will generate a polymer.

The term "alkylene having at least 8 carbon atoms in the chain" means a straight chain or branched chain alkylene group having the stated minimum number of carbon atoms directly linked together in the chain. Illustrative of such groups are octylene, decylene, undecylene, 2,3-dimethylundecylene, 5-methylundecylene, dodecylene, 4-methyldodecylene, tridecylene, 5,6-dimethyltridecylene, tetradecylene, pentadecylene, hexadecylene, octadecylene and the like, including isomeric forms thereof. The upper limit of carbon atoms in the chain, and the total number of carbon atoms in the group, are not critical and are governed only by availability of the appropriate starting compounds to be described hereafter. Generally speaking, however, the maximum number of carbon atoms in the chain is of the order of 18.

The above various alkylene groups can be unsubstituted or can be substituted by one or more groups which are inert, i.e. unreactive towards isocyanate groups and towards active hydrogen containing groups. Such substituents include alkoxy such as methoxy, ethoxy, propoxy, butoxy, pentyloxy, hexyloxy and isomeric forms thereof; alkenyl such as allyl, butenyl, pentenyl, hexenyl and isomeric forms thereof; alkenyloxy such as allyloxy, butenyloxy, pentenyloxy, hexenyloxy and isomeric forms thereof; cyano; halogen; and alkylmercapto such as methylmercapto, ethylmercapto, propylmercapto, butylmercapto, pentylmercapto, hexylmercapto and isomeric forms thereof.

DETAILED DESCRIPTION OF THE INVENTION

The compounds of formula (I) can be prepared readily by cyclization of the appropriate allophanoyl halide of the formula:

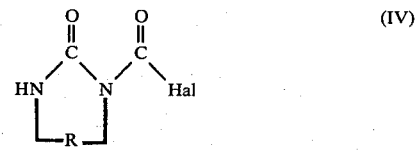

wherein R is as above defined and Hal is chlorine or bromine. The cyclization is accomplished by reacting the allophanoyl halide with a scavenger for hydrogen halide. Advantageously, the cyclization is carried out in the presence of an inert organic solvent, i.e. a solvent which does not enter into reaction with the other components of the reaction mixture or interfere in any way with the desired course of the reaction. Illustrative of inert organic solvents are benzene, toluene, xylene, chloroform, methylene chloride, chlorobenzene, dimethylformamide, tetrahydrofuran and the like. The scavenger for hydrogen halide employed in the process of the invention can be any of the various compounds known in the art to act as acceptors of hydrogen halide. Illustrative of such scavengers are tertiary amines of which the following are representative:- trimethylamine, triethylamine, tripropylamine, tributylamine, collidine, dimethylaniline, diethylaniline, pyridine, N-methylpiperidine, N,N'-dimethylpiperazine, and the like.

In most instances the cyclization proceeds readily at ambient temperatures, i.e. temperatures of the order of about 15°–25° C. but elevated temperatures can be employed if desired. Thus, temperatures up to 80° C. or even higher can be employed provided that the reaction temperature in any given instance must obviously be less than the temperature at which the compound (I) will be converted to the corresponding diisocyanate (II).

The reaction product obtained by the above cyclization is generally a mixture of the desired compound (I) and the corresponding diisocyanate (II). The mixture can be separated into its components by conventional procedures such as chromatography, fractional crystallization and the like.

The allophanoyl halides (IV) which are employed in the preparation of the compounds (I) of the invention can be prepared by any of a number of methods well-known in the art. Illustratively, the allophanoyl halides (IV) are prepared by reaction of the corresponding cyclic ureas of the formula:

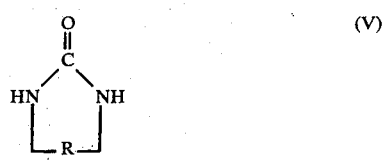
(V)

wherein R has the significance defined above, with phosgene or carbonyl bromide using the procedure described, for example, in U.S. Pat. No. 3,275,618. The cyclic ureas (V) which are employed as starting materials in the above reaction are for the most part known compounds which can be obtained readily by methods known in the art; see, for example U.S. Pat. No. 4,138,398.

Alternatively, the allophanoyl halides (IV) can be prepared by reaction of phosgene with the appropriate carbodiimide of the formula:

(VI)

where R has the significance hereinbefore defined. The conditions employed in the reaction can be, for example, those described by Greene et al., J. Organic Chemistry 43, 4530 (1978), for the preparation of acyclic allophanoyl halides from the corresponding carbodiimides. The carbodiimides (VI) which are employed as starting materials in the above process can be obtained from the corresponding lactams (2-azacycloalkanones) using the procedure described by Damrauer et al., J. Organic Chemistry, 45, 1316 (1980). This method of preparation is illustrated below in Example 1. The carbodiimides (VI) can be prepared by the reaction of the corresponding cyclic thiourea of the formula:

(VII)

where R is as hereinbefore defined, with mercuric oxide using the procedure described by Hiatt et al., J. Organic Chemistry, 44, 3265 (1979). The latter reference also describes a process which can be employed for the preparation of the thioureas (VII) from the corresponding diamines $H_2N-R-NH_2$.

The compounds of the invention of the formula (I) are, for the most part, crystalline solids which remain stable, i.e. show no sign of dissociating to form the diisocyanates (II), when maintained indefinitely at ambient temperatures i.e. 15° to 25° C. However, when the compounds (I) are heated to temperatures of the order of about 100° C. or higher, they dissociate readily to form the corresponding diisocyanates (II) in substantially quantitative yield. This property of the compounds (I) renders them extremely useful as "masked diisocyanates" in "one-can" polyurethane systems. Thus the compounds of formula (I) can be blended with substantially stoichiometric proportions of a polyol or mixture of polyols and the mixture can be stored indefinitely at ambient temperatures. At any desired time the mixture can be heated to temperatures in the range of about 100° C. to 170° C. whereupon the compound of formula (I) is converted to the corresponding diisocyanate (II) and reaction of the latter with the polyol ensues resulting in the formation of a polyurethane.

If desired, the storage stable mixture of the compound of formula (I) and polyol can also include a catalyst, a low molecular weight extender such as an alkanediol, and or any of the other additives such as fire retardants, fillers, pigments and the like commonly employed in the formation of polyurethanes. The catalyst, if used, can be any of the catalysts commonly employed in the reaction of an isocyanate and an active-hydrogen group containing compound. Representative of such catalysts are stannous octoate, stannous oleate, dibutyltin dioctoate, dibutyltin dilaurate, and tertiary amines such as triethylamine, triethylenediamine, N-methylmorpholine, N,N-dimethylethanolamine and the like.

The above "one-can" systems which incorporate the compounds of formula (I) can be employed, for example, as coating compositions particularly for wire coating and for coating of metals in general, and as molding compositions for the production of seals, gaskets, and the like, as well as for potting purposes. Depending upon thenature and functionality of the polyol utilized in the "one-can" systems the resulting polyurethane will be rigid or elastomeric. Thus, by utilizing a polymeric glycol as the polyol and employing a low molecular weight glycol as extender the "one-can" system can be utilized to prepare elastomeric polyurethanes. By utilizing a polyol having a functionality of three or higher the "one-can" system can be used to prepare a rigid polyurethane.

As pointed out above, allophanoyl halides corresponding to those illustrated in formula (IV) but having alkylene chains (R) with up to 4 carbon atoms only have been described in the art. We have found that it is not possible to convert such allophanoyl halides into the corresponding diazetidinediones-2,4. Indeed we have found that it appears to be necessary to have at least 8 carbon atoms in the chain represented by R in formula (IV) before it is possible to produce the corresponding diazetidinediones-2,4 of formula (I). While there is a requirement to have such a minimum number of carbon atoms present in the chain there is no maximum number beyond which it is not possible to form the diazetidinediones. Thus the upper limit on the number of carbon atoms in the chain of the group R in formula (I) and (IV) is governed only by the availability of the requisite starting materials used to prepare these compounds.

The following examples describe the manner and process of making and using the invention and set forth the best mode contemplated by the inventors of carrying out the invention but are not to be construed as limiting.

EXAMPLE 1

(a) 1-azacyclotridecanone-2-oxime.

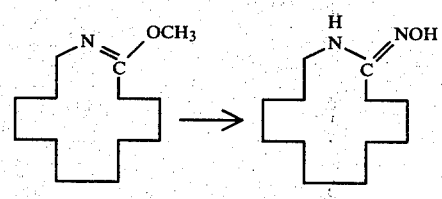

A total of 105.5 g. (0.5 mole) of 2-methoxy-1-azacyclotridec-1-ene [prepared as described in German Offenlegungsschrift 2012434 (1970), from lauryl lactam and dimethyl sulfate] was added dropwise over a period of 20 minutes to a mixture of 40 g. (0.57 mole) of hydroxylamine hydrochloride and 60 g. (0.71 mole) of sodium bicarbonate in 500 ml. of methanol. Vigorous evolution of carbon dioxide occurred during the addition. When this evolution had subsided the resulting suspension was heated under reflux for 1.5 hr. before being filtered while still hot. The filtrate was allowed to stand overnight at circa 0° C. The solid which had separated was isolated by filtration and a second crop of crystals was obtained by concentrating the filtrate and allowing the concentrate to stand at circa 0° C. There was thus obtained a total of 81.25 g. (77% yield) of 1-azacyclotridecanone-2 oxime in the form of a crystalline solid (colorless needles) having a melting point of 123°–125° C.

(b) O-methanesulfonate of 1-azacyclotridecanone-2 oxime.

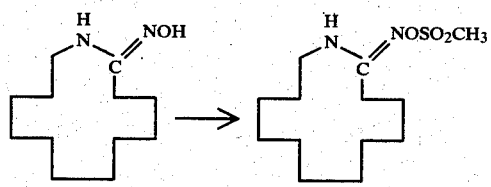

To a cooled suspension of 42.4 g. (0.2 mole) of 1-azacyclotridecanone-2 oxime (prepared as described above) in 200 ml. of pyridine was added, dropwise over a period of 15 minutes, a total of 24 g. (0.21 mole) of methanesulfonyl chloride. The resulting mixture initially formed a clear solution which later deposited a thick precipitate. The mixture was initially stirred for 30 minutes while cooled in ice and later was stirred without cooling until deposition of precipitate made stirring impossible. At this time (2 hr. after initial mixing) the suspension was diluted with circa 500 ml. of water and the precipitate was isolated by filtration, washed thoroughly with water, and dried in air. There was thus obtained 52.2 g. (90% yield) of the O-methanesulfonate of 1-azacyclotridecanone-2 oxime in the form of a solid.

(c) 1,3-diazacyclotetradeca-1,2-diene.

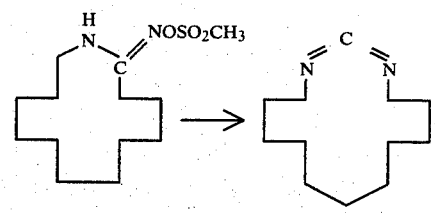

To a suspension of 7 g. of potassium t-butoxide in 70 ml. of 1,2-dimethoxyethane was added slowly, with stirring, a total of 14.5 g. (0.05 mole) of the O-methanesulfonate of 1-azacyclotridecanone-2 oxime (prepared as described above). An exothermic reaction occurred. After the addition was complete the reaction mixture was stirred for a further 45 minutes after being filtered. The isolated solid was washed on the filter with 1,2-dimethoxyethane and the combined filtrate and washings were evaporated to leave an oil. The latter was taken up in a mixture of water and methylene chloride. The methylene chloride layer was separated, washed twice with water, dried over anhydrous sodium sulfate and evaporated to dryness. The residue was distilled in vacuo to yield 8.3 g. (87% yield) of 1,3-diazacyclotetradeca-1,2-diene in the form of an oil having a boiling point of 90° to 95° C. at a pressure of 0.01 mm. of mercury. A sample of this material prepared in a different run was found to have the following analysis:

Calcd. for $C_{12}H_{22}N_2$: C, 74.17; H, 11.41; N, 14.42%; Found: C, 74.33; H, 10.92; N, 15.14%.

(d) 1,3-diazacyclotetradecan-2-one-1-carbonyl chloride

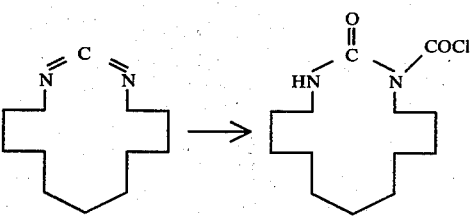

A solution of 9.7 g. (0.05 mole) of 1,3-diazacyclotetradeca-1,2-diene (prepared as described above) in 20 ml. of methylene chloride was added slowly with stirring to a solution of 15 g. (0.15 mole) of phosgene in 50 ml. of methylene chloride cooled in ice. An exothermic reaction ensued and an infrared spectrum taken a few minutes after the addition was complete indicated that the desired reaction has proceeded to completion. The solvent was removed by distillation and the liquid residue was dissolved in 30 ml. of acetone. Approximately 4 ml. of water was added to the acetone solution. The resulting mixture was slightly turbid and sufficient acetone was added to give a clear solution. The latter was allowed to stand for 21 hr. at circa 20° C. before removing the solvent by distillation. The solid residue (13.43 g: 97% yield) was recrystallized from hexane to give 1,3-diazacyclotetradecan-2-one-1-carbonyl chloride in the form of colorless crystals. A sample produced in a duplicate run had a melting point of 65°–67° C. and the following analysis:

Calcd. for $C_{15}H_{23}ClN_2O_2$: C, 56.82; H, 8.44; N, 10.19; Cl,12.90%; Found: C, 57.06; H, 8.26; N, 10.16; Cl,13.10%.

(e) 1,3-undecylene-diazetidinedione-2,4

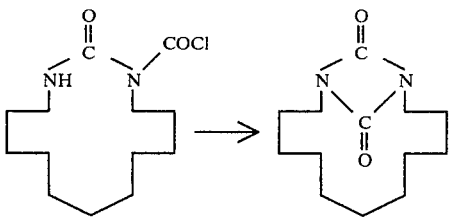

A solution containing 8.25 g. (0.03 mole) of 1,3-diazacyclotetradecan-2-one-1-carbonyl chloride and 10 g. (0.1 mole) of triethylene in 100 ml. of chloroform was allowed to stand at room temperature (circa 20° C.) for 8 days (at the end of 7 days a further 2 g. of triethylamine was added) until the reaction was adjudged complete by reason of disappearance of the absorption band for C=O in the infrared spectrum of an aliquot. The solvent was removed by distillation and the solid which remained was dissolved in n-hexane. The suspension was filtered and the insoluble material was washed on the filter with n-hexane. The filtrate was concentrated and cooled in ice. The crystalline material which separated was isolated by filtration, washed with n-hexane, and dried to give 0.95 g. of 1,3-undecylene-diazetidined-ione-2,4 in the form of colorless crystals having a melting point of 93° to 94° C. A sample obtained in a duplicate experiment had the following analysis:

Calcd. for $C_{13}H_{22}N_2O_2$: C, 65.51; H, 9.31; N, 11.76%; Found: C, 65.66; H, 9.43; N, 11.76%.

EXAMPLE 2

A solution of 0.1 g. of 1,3-undecylene-diazetidined-ione-2,4 in 2 ml. of o-dichlorobenzene was placed in an oil bath preheated to 160°-165° C. The progress of the reaction was followed by infrared spectroscopic analysis of aliquots. After 7 hrs. only a trace of the starting material was still present and the solution contained only 1,11-diisocyanatoundecane.

EXAMPLE 3

1,3-decylene-diazetidinedione-2,4.

(a) 1-azacyclododecanone-2 oxime

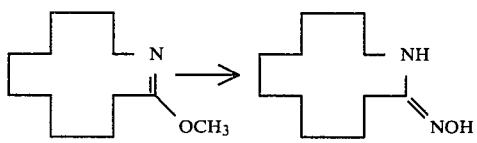

A total of 68 g. (0.345 mole) of 2-methoxy-1-azacyclododec-1-ene (German Offenlegungschrift No. 2012434, 1970) was added dropwise with stirring to a mixture of 25 g. (0.36 mole) of hydroxylamine hydrochloride and 35 g. (0.415 mole) of sodium bicarbonate in 350 ml. of methanol. The addition was completed in 60 minutes at ambient temperature (circa 20° C.). The resulting mixture was heated at 55° to 60° C. with stirring for approximately 3 hours. The mixture so obtained was then filtered, the filtrate concentrated in vacuo and cooled to ambient temperature, leaving a bluish oil which solidified. The solid was again dissolved in methanol and the solution was diluted with water. The oil which was formed initially turned solid and was isolated by filtration. The solid was contaminated by a small amount of a bluish material and was therefore dissolved in 500 ml. of n-hexane and heated under reflux. The bluish material remained undissolved and the mixture was decanted through glass wool to separate the clear supernatant from the insoluble bluish material. The solution so obtained was evaporated to dryness to yield a residue of 48 g. of 1-azacyclododecanone-2 oxime as a colorless solid.

(b) 1,3-diazacyclotrideca-1,2-diene

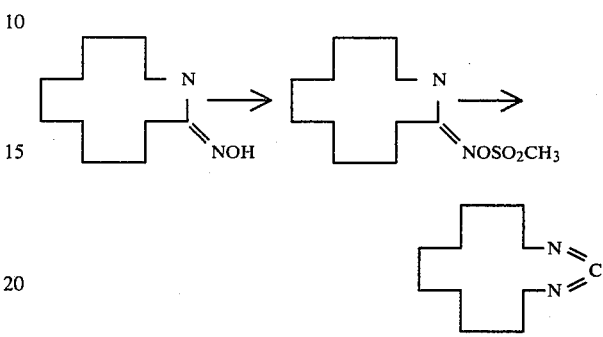

To an ice-cold suspension of 10 g. (0.05 mole) of 1-azacyclododecanone-2 oxime in 25 ml. of pyridine was added, dropwise with stirring, a total of 6 g. (0.052 mole) of methanesulfonyl chloride over a period of 5 minutes. When the addition was complete, a precipitate of colorless crystals separated from the solution. The reaction product was stirred for a further 50 minutes in an ice-bath before being decomposed by the addition of 50 ml. of water. The aqueous layer was decanted from the yellow oil which separated and the latter was washed by decantation using three successive portions of water. The remaining yellow oil (the methane sulfonate of the starting oxime) was dissolved in 50 ml. of methylene chloride and the resulting solution was admixed with a solution of 10 g. of potassium hydroxide in 100 ml. of water and stirred vigorously for 1.5 hr. at room temperature (circa 20° C.). At the end of this period the methylene chloride solution was separated and washed with water and dried over anhydrous sodium sulfate. The dried solution was evaporated to dryness and the residue was extracted with n-hexane. The n-hexane solution was separated from an insoluble brown resin and evaporated to dryness. The residue was distilled in vacuo to yield 2.1 g. of 1,3-diazacyclotrideca-1,3-diene as an oil having a boiling point of 84° C. at 0.1 mm. of mercury.

Anal. Calcd. for $C_{11}H_{20}N_2$: C, 73.28; H, 11.18; N, 15.54; Found: C, 73.40; H, 11.40; N, 15.65.

(c) 1,3-diazacyclotridecan-2-one-1-carbonyl chloride

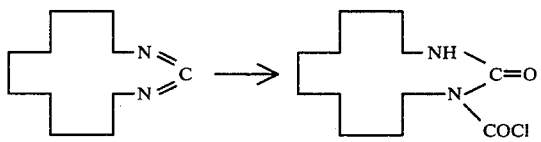

A solution of 6 g. (0.06 mole) of 1,3-diazacyclotrideca-1,2-diene in 25 ml. of methylene chloride was added slowly with stirring to a solution of 13 g. (0.13 mole) of phosgene in 25 ml. of methylene chloride which latter was cooled in an ice bath. An exothermic reaction ensued. The mixture was stirred for a further 20 minutes, with cooling, after the addition was complete and then the methylene chloride and phosgene were removed by evaporation. The oily residue was dissolved in acetone and a small amount of water (just sufficient to avoid turbidity) was added. The resulting mixture was allowed to stand overnight before being diluted with an excess of water. The oil which separated initially solidified and was isolated by filtration, washed with water and dried. There was thus obtained 7.2 g. (82 percent yield) of 1,3-diazacyclotridecan-2-one-1-carbonyl chloride. A sample was recrystallized from n-hexane to yield colorless crystals having a melting point of 72° C.

Anal.: Calcd. for $C_{12}H_{21}ClN_2O_2$: C, 55.28; H, 8.11; Cl, 13.60; N, 10.74; Found: C, 55.24; H, 8.17; Cl, 13.56; N, 10.74.

(d) 1,3-decylene-diazetidinedione-2,4

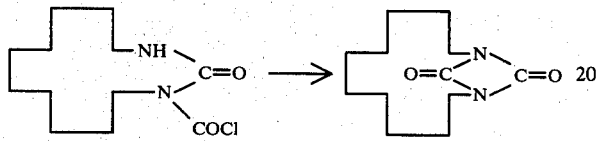

A solution containing 6.9 g. (0.0265 mole) of 1,3-diazacyclotridecan-2-one-1-carbonyl chloride and 10 g. of triethylamine in 100 ml. of chloroform was allowed to stand at room temperature (circa 20° C.) (after 100 hr. a further 2 g. of triethylamine was added) until the reaction was adjudged complete by reason of disappearance of the absorption band for C═O of the carbonyl chloride in the infrared spectrum of an aliquot. The resulting brown solution was evaporated to dryness and the semi-solid residue was taken up in approximately 100 ml. of n-hexane. After shaking for a few minutes the solution was filtered and the insoluble material was washed with n-hexane. The filtrate and washings are concentrated by evaporation and the concentrate was cooled in ice. The solid (0.39 g.) which separated was isolated by filtration and recrystallized from methanol to yield 1,3-decylene-diazetidinedione-2,4 in the form of colorless needles having a melting point of 98° to 99° C.

Anal. Calcd. for $C_{12}H_{20}N_2O_2$ (M.W. 224): C, 64.25; H, 8.99; N, 12.49; Found: C, 64.52; H, 9.07; N, 12.51; Molecular Weight (Found): 226(CHCl$_3$).

We claim:

1. A compound having the formula:

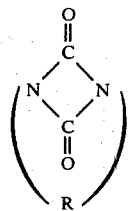

wherein R is alkylene having from 8 to 18 carbon atoms in the chain.

2. A compound according to claim 1 wherein R represents —(CH$_2$)$_{11}$— said compound being 1,3-undecylene-diazetidinedione-2,4.

3. A compound according to claim 1 wherein R represents —(CH$_2$)$_{10}$— said compound being 1,3-decylene-diacetidinedione-2,4.

4. A storage stable composition which will generate a polyurethane upon heating to a temperature of at least about 100° C., which composition comprises a compound according to claim 1 and a polyol wherein the polyol is present in an amount corresponding to approximately 2 equivalents per molar proportion of the compound according to claim 1.

5. A storage stable composition according to claim 4 wherein the compound according to claim 1 is that in which R represents —(CH$_2$)$_{11}$—.

6. A storage stable composition according to claim 4 wherein the compound according to claim 1 is that in which R represents —(CH$_2$)$_{10}$—.

7. A storage stable composition according to claim 4 which also comprises a catalyst for the reaction between isocyanate and active-hydrogen containing groups.

* * * * *

UNITED STATES PATENT OFFICE
CERTIFICATE OF CORRECTION

Patent No. 4,339,381  Dated July 13, 1982

Inventor(s) Reinhard H. Richter, Benjamin W. Tucker and Henri Ulrich

It is certified that error appears in the above-identified patent and that said Letters Patent are hereby corrected as shown below:

Column 4, line 43 "themature" should read --the nature--.
Column 5, line 9 "1-azacyclotridecanone-2-oxime" should read --1-azacyclotridecanone-2 oxime--. Column 6, line 52 "has" should read --had--. Column 7, line 14 "triethylene" should read --triethylamine--. Column 9, line 36 "are" should read --were--.

Signed and Sealed this

Eighteenth Day of January 1983

[SEAL]

Attest:

Attesting Officer

GERALD J. MOSSINGHOFF

Commissioner of Patents and Trademarks